United States Patent [19]

Locatell, Jr. et al.

[11] Patent Number: 4,619,784

[45] Date of Patent: * Oct. 28, 1986

[54] IMAGE DYE-PROVIDING MATERIALS

[75] Inventors: Louis Locatell, Jr., Wellesley; Charles M. Zepp, Boylston; Ronald F. Cieciuch, Brookline, all of Mass.

[73] Assignee: Polaroid Corporation, Patent Dept., Cambridge, Mass.

[*] Notice: The portion of the term of this patent subsequent to Sep. 20, 2000 has been disclaimed.

[21] Appl. No.: 200,953

[22] Filed: Oct. 27, 1980

Related U.S. Application Data

[62] Division of Ser. No. 106,506, Dec. 26, 1979, Pat. No. 4,267,251.

[51] Int. Cl.$^4$ .............. C07D 209/12; C07D 215/14; C07D 223/16
[52] U.S. Cl. .................. 540/593; 546/165; 548/181; 548/490; 548/491; 430/224; 430/243; 540/476
[58] Field of Search ........... 548/181, 490, 491; 430/224, 243; 546/165; 260/336, 239 PB

[56] References Cited

U.S. PATENT DOCUMENTS

| | | | |
|---|---|---|---|
| 3,883,529 | 12/1972 | Austin | 260/336 |
| 3,956,300 | 8/1974 | Austin | 260/249.5 |
| 4,237,281 | 12/1980 | Long | 544/99 |
| 4,264,507 | 4/1981 | Borror | 260/336 |
| 4,285,859 | 8/1981 | Kitzing | 260/155 |

FOREIGN PATENT DOCUMENTS

| | | | |
|---|---|---|---|
| 2907437 | 8/1978 | Fed. Rep. of Germany | 260/336 |
| 5050244 | 10/1978 | Japan | 260/336 |
| 1423346 | 2/1972 | United Kingdom | 260/336 |
| 2016031 | 9/1979 | United Kingdom | 260/336 |

OTHER PUBLICATIONS

Ramanauskas, E., et al., Chem. Abst., vol. 88: 192734d.

*Primary Examiner*—Glenna M. Hendricks
*Attorney, Agent, or Firm*—Gaetano D. Maccarone

[57] ABSTRACT

There are disclosed diffusion transfer color processes and products which employ novel image dye-providing materials which provide image dyes having the chromophoric system represented by the formula

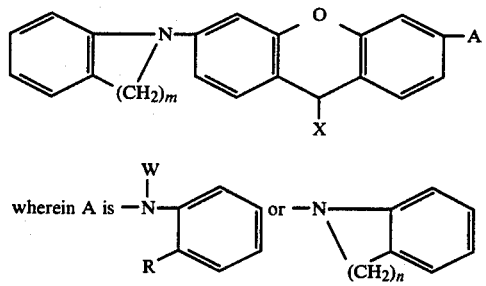

X is H, alkyl, aryl or substituted aryl; W is H or alkyl, R is H or alkyl; m and n are each integers of from 2 to 6.

The image dye-providing material includes a diffusion control moiety such as a hydroquinonyl group and may be diffusible or nondiffusible as a function of the diffusion control moiety.

12 Claims, 1 Drawing Figure

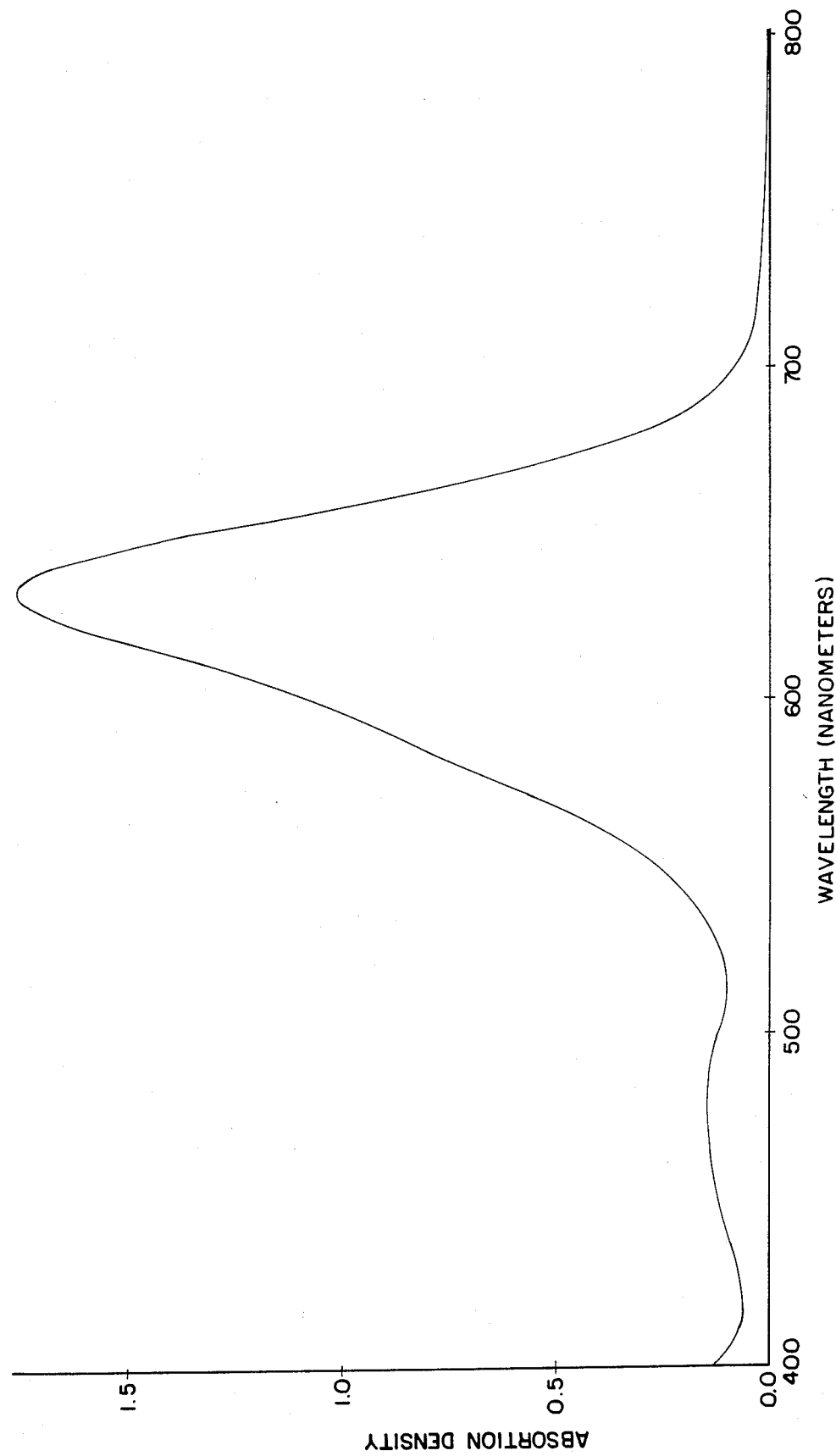

IMAGE DYE-PROVIDING MATERIALS

CROSS REFERENCE TO RELATED APPLICATIONS

This application is a division of prior copending application Ser. No. 106,506, filed Dec. 26, 1979 now U.S. Pat. No. 4,267,251.

BACKGROUND OF THE INVENTION

This invention relates to photography in general and, more particularly, to dyes which are useful in providing diffusion transfer color images and to photographic products and processes employing such dyes.

Multicolor images formed in accordance with the principles of subtractive color photography employ yellow, magenta and cyan image dyes. The yellow dye ideally transmits only green and red light and absorbs only blue light, and thus is sometimes referred to as "minus blue". In like manner, the magenta ("minus green") dye ideally absorbs only green light and transmits only blue and red light, and the cyan ("minus red") dye ideally absorbs only red light and transmits only blue and green light. Unfortunately, the dyes available for use in subtractive color photography are not "ideal" dyes, but tend to absorb some of the light that they ideally should transmit. This extra absorption results in less effective reproduction by the final image of one or more colors present in the original subject.

This problem may be illustrated by considering the reproduction of blue light: a multicolor photosensitive element, containing a blue-sensitive silver halide layer, a green-sensitive silver halide layer and a red-sensitive silver halide layer, said silver halide layers having associated therewith, respectively, a yellow image dye-providing material, a magenta image dye-providing material, and a cyan image dye-providing material, is exposed to blue light in an amount effective to fully expose the blue-sensitive layer. Only the blue-sensitive silver halide layer is exposed; the green-sensitive and red-sensitive silver halide emulsion layers remain unexposed. If such an exposed photosensitive element were processed by diffusion transfer techniques, the yellow image dye-providing material would remain in the developed photo-sensitive element (negative component) but magenta and cyan image dyes would be transferred to the image-receiving layer (positive component). Since the magenta and cyan image dyes are "minus green" and "minus red" respectively, the *combination* and magenta and cyan dyes appear blue, i.e., they transmit blue light to the viewer and absorb green and red, thus reproducing the blue record of the original object.

In the art of photography there is a continuing search for new image-forming dyes. The present application is drawn to novel image dye-providing materials which are useful in photography.

SUMMARY OF THE INVENTION

It is therefore the object of this invention to provide novel compounds.

It is another object to provide image-forming dyes which are useful in photography.

It is a further object to provide dye developers which are useful in photographic diffusion transfer applications.

Still another object is to provide image dye-providing materials which are useful in dye release diffusion transfer processes, for example of the redox dye release or the silver-catalyzed dye release types.

Yet another object is to provide novel photographic products and processes.

A further object is to provide novel diffusion transfer photographic products and processes.

BRIEF SUMMARY OF THE INVENTION

These and other objects and advantages are accomplished in accordance with the invention by providing materials which provide image dyes having the chromophoric system represented by the formula

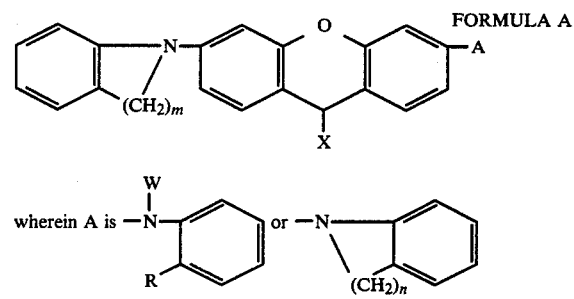

FORMULA A wherein A is

X is H, alkyl, preferably having from 1 to 6 carbon atoms, aryl such as phenyl or naphthyl, or aryl substituted with substituents such as $SO_3^\ominus$, $CO_2^\ominus$, or alkyl, preferably having from 1 to 6 carbon atoms; W is H or alkyl, preferably having from 1 to 6 carbon atoms; R is H or alkyl, preferably having from 1 to 6 carbon atoms; m and n are each integers of from 2 to 6.

It will be understood that compounds within Formula A may be represented by the resonance form such as, for example,

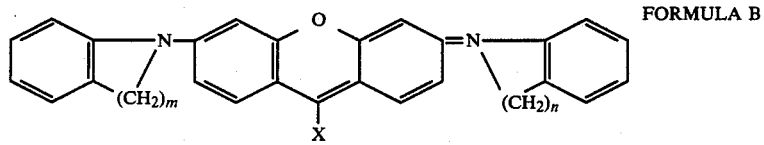

FORMULA B

Both resonance forms of the chromophoric system are intended to be encompassed by Formula A.

In a preferred embodiment X is

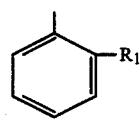

wherein $R_1$ is H, $SO_3^\ominus$, $CO_2^\ominus$ or alkyl, preferably alkyl having from 1 to 6 carbon atoms. $R_1$ is preferably $SO_3^\ominus$ since such compounds typically exhibit good stability in alkali.

The image dye-providing materials include a diffusion control moiety such as a hydroquinonyl group and may be diffusible or nondiffusible as a function of the diffusion control moiety.

In the photographic diffusion transfer processes of the invention the desired image is obtained by processing an exposed photosensitive silver halide material with a processing composition distributed between two sheet-like elements, one of said elements including said photosensitive material. The processing composition is so applied and confined within and between the two sheet-like elements as not to contact or wet outer surfaces of the superposed elements, thus providing a film unit or film packet whose outer surfaces are dry. The processing composition may be viscous or nonviscous and preferably is distributed from a single-use container; such pressure rupturable processing composition containers are frequently referred to as "pods". The final image may be monochrome or multicolor and is formed in an image-receiving layer included in one of said sheet-like elements.

As is well known in diffusion transfer photography, the image dye-providing materials which may be utilized in such processes generally may be characterized as either (1) initially soluble or diffusible in the processing composition but which are selectively rendered nondiffusible imagewise as a function of development; or (2) initially insoluble or nondiffusible in the processing composition but which selectively provide a diffusible product imagewise as a function of development. The image dye-providing materials may be complete dyes or dye intermediates, e.g., color couplers. The requisite differential in mobility or solubility may, for example, be obtained by a chemical reaction such as a redox reaction, a coupling reaction or a cleavage reaction.

The image dye providing materials which are capable of providing image dyes containing the chromophoric system of Formula A may be provided by including a diffusion control substituent, Y, which substituent includes a diffusion control moiety, D. One such group of image dye-providing materials is represented by the formula

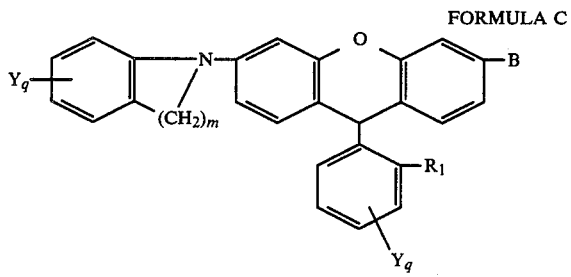

FORMULA C

-continued

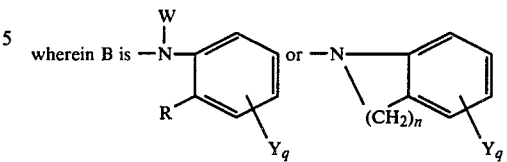

each Y is a substituent containing a diffusion control moiety, and each q is 0 or 1 provided that at least one q is 1.

In such image dye-providing materials the diffusion control substituent may be represented by —E—Dev wherein Dev is a hydroquinonyl group and E is a covalent bond or a divalent linking group, for example, alkylene.

Image dye-providing materials within Formula C, as a function of the particular diffusion control moiety D which is present, are suitable for use in diffusion transfer processes employing either initially diffusible or initially nondiffusible image dye-providing materials. Typical diffusion control moieties include hydroquinonyl groups, color coupling groups, sulfonamido phenol groups which cleave or ring close following oxidation to release a diffusible dye or dye intermediate, and thiazolidine groups whose cleavage is silver catalyzed. The diffusion control moiety D may be attached by a covalent bond or a divalent organic radical, for example, an alkylene radical, to complete the diffusion control substituent Y. Further, where the image dye-providing material is initially diffusible a suitable ballast group, for example, a long chain alkyl group, may be attached to the diffusion control moiety.

BRIEF DESCRIPTION OF THE DRAWING

For a better understanding of the invention as well as other objects and advantages of the invention and further features thereof, reference is made to the following detailed description of various preferred embodiments thereof taken in conjunction with the drawing wherein the FIGURE is the absorption specturm of one of the preferred image dye-providing materials of the invention.

DESCRIPTION OF THE PREFERRED EMBODIMENT

Preferred image dye-providing materials of the invention are represented by the formulas:

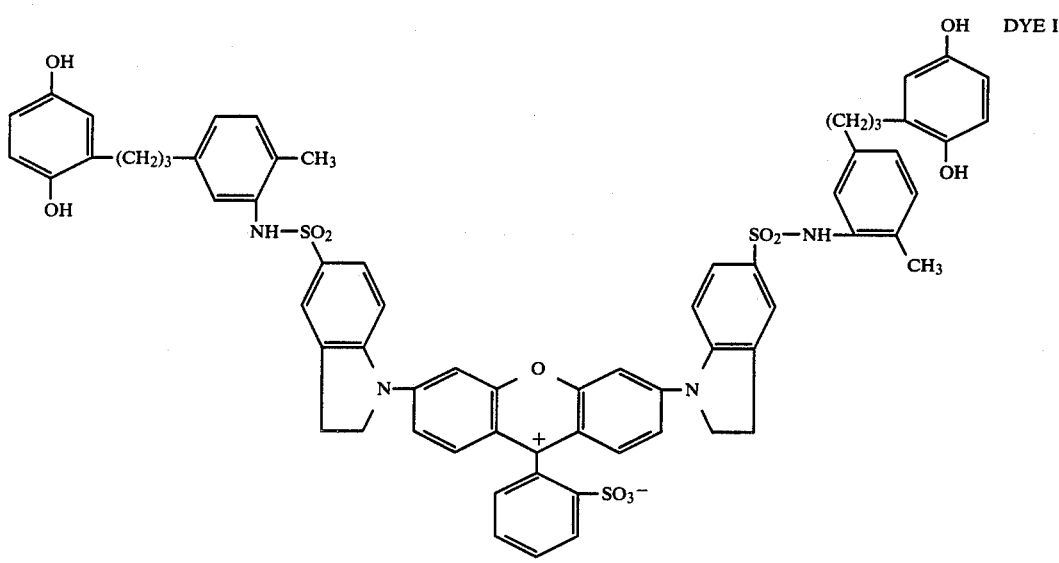
DYE I
The FIGURE illustrates the absorption spectrum of dye I as obtained from a $2\times10^{-5}$ molar solution in methyl cellosolve. The dye has a $\lambda$ max = 632 nm and $\epsilon = 87,500$.
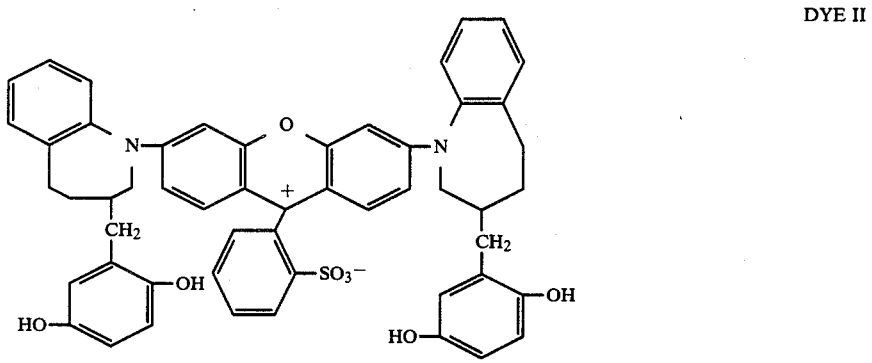
DYE II
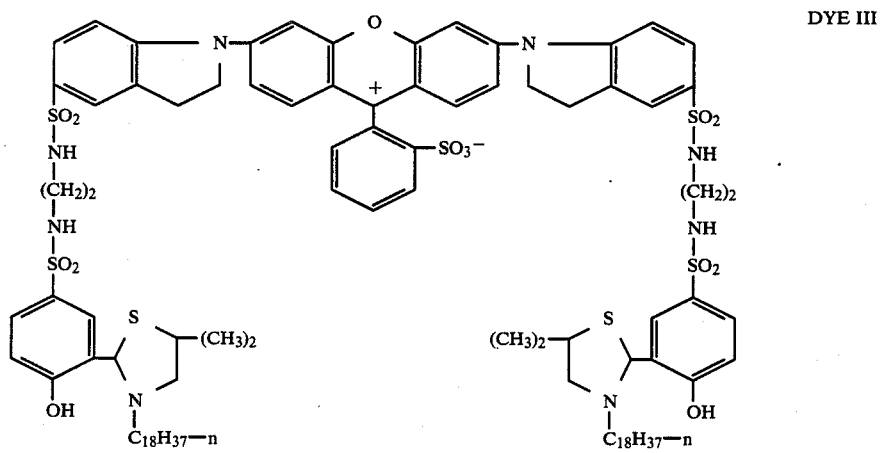
DYE III -continued
DYE IV
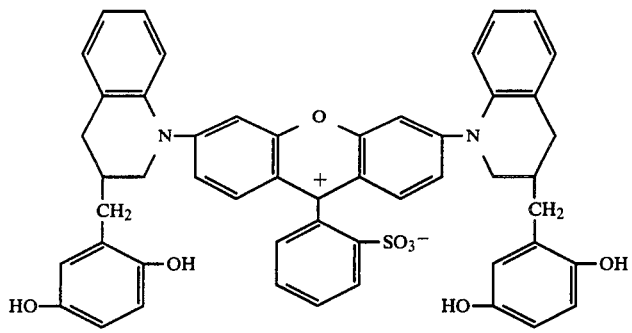
DYE V
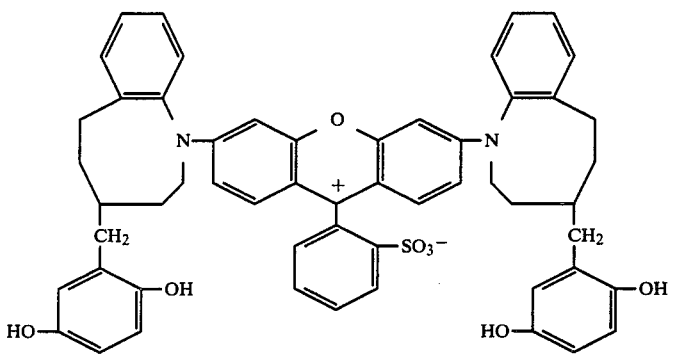
DYE VI
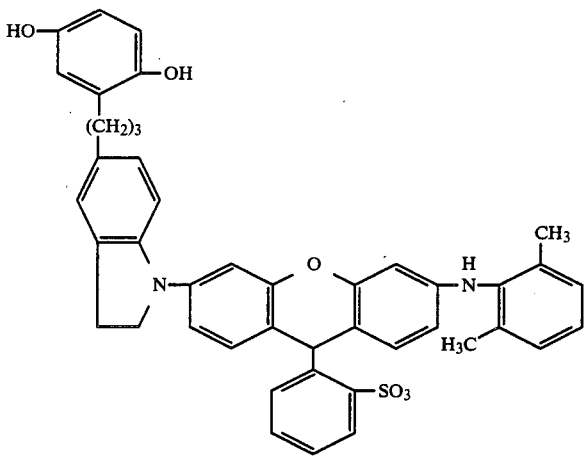
DYE VII
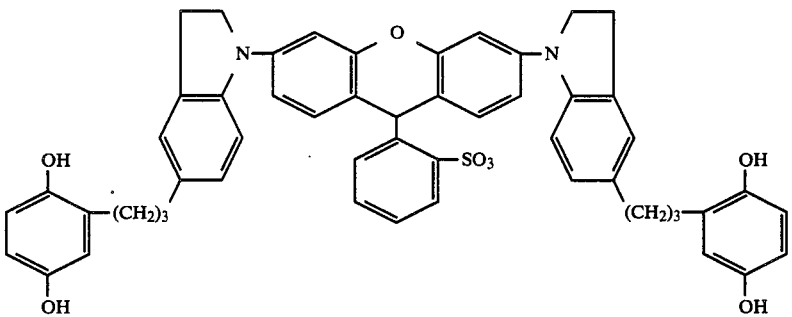
The image dye-providing materials of the invention are of various colors. For example, within Formula A, when A is
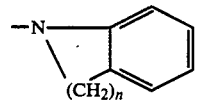

and m and n are each 2, the compounds are typically cyan in solution and in a photograph and when m and n are each 3 the compounds are typically blue in solution and in photographs; when m and n are each 4 or 5 the compounds typically are magenta in solution and in photographs.

In a particularly preferred embodiment of the invention the diffusion control moiety is a hydroquinonyl moiety and the resulting dye developers are initially diffusible image dye-providing materials. As described in U.S. Pat. No. 2,983,606 a photosensitive element containing a dye developer and a silver halide emulsion is photoexposed and a processing composition applied thereto, for example, by immersion, coating, spraying, flowing, etc., in the dark. The exposed photosensitive element is superposed prior to, during, or after the processing composition is applied, on a sheet-like support element which may be utilized as an image-receiving element. In a preferred embodiment, the processing composition is applied to the exposed photosensitive element in a substantially uniform layer as the photosensitive element is brought into superposed relationship with the image-receiving layer. The processing composition, positioned intermediate the photosensitive element and the image-receiving layer, permeates the emulsion to initiate development of the latent image contained therein. The dye developer is immobilized or precipitated in exposed areas as a consequence of the development of the latent image. This immobilization is apparently, at least in part, due to a change in the solubility characteristics of the dye developer upon oxidation and especially as regards its solubility in alkaline solutions. It may also be due in part to a tanning effect on the emulsion by oxidized developing agent, and in part to a localized exhaustion of alkali as a result of development. In unexposed and partially exposed areas of the emulsion, the dye developer is unreacted and diffusible and thus provides an imagewise distribution of unoxidized dye developer, diffusible in the processing composition, as a function of the point-to-point degree of exposure of the silver halide emulsion. At least part of this imagewise distribution of unoxidized dye developer is transferred, by imbibition, to a superposed image-receiving layer or element, said transfer substantially excluding oxidized dye developer. The image-receiving layer receives a depthwise diffusion, from the developed emulsion, of unoxidized dye developer without appreciably disturbing the imagewise distribution thereof to provide a reversed or positive color image of the developed image. The image-receiving element may contain agents adapted to mordant or otherwise fix the diffused, unoxidized dye developer. In a preferred embodiment of said U.S. Pat. No. 2,983,606 and in certain commercial applications thereof, the desired positive image is revealed by separating the image-receiving layer from the photosensitive element at the end of a suitable imbibition period. Alternatively, as also disclosed in said U.S. Pat. No. 2,983,606, the image-receiving layer need not be separated from its superposed contact with the photosensitive element, subsequent to transfer image formation, if the support for the image-receiving layer, as well as any other layers intermediate said support and image-receiving layer, is transparent and a processing composition containing a substance, e.g., a white pigment, effective to mask the developed silver halide emulsion or emulsions is applied between the image-receiving layer and said silver halide emulsion or emulsions.

Dye developers, as noted in said U.S. Pat. No. 2,983,606, are compounds which contain, in the same molecule, both the chromophoric system of a dye and also a silver halide developing function. By "a silver halide developing function" is meant a grouping adapted to develop exposed silver halide. A preferred silver halide development function is a hydroquinonyl group. In general, the development function includes a benzenoid developing function, that is, an aromatic developing group which forms quinonoid or quinone substances when oxidized.

Multicolor images may be obtained using dye developers in diffusion transfer processes by several techniques. One such technique contemplates obtaining multicolor transfer images utilizing dye developers by employment of an integral multilayer photosensitive element, such as is disclosed in the aforementioned U.S. Pat. No. 2,983,606 and in U.S. Pat. No. 3,345,163, wherein at least two selectively sensitized photosensitive strata, superposed on a single support, are processed, simultaneously and without separation, with a single common image-receiving layer. A suitable arrangement of this type comprises a support carrying a red-sensitive silver halide emulsion stratum, a green-sensitive silver halide emulsion stratum and a blue-sensitive silver halide emulsion stratum, said emulsions having associated therewith, respectively, for example, a cyan dye developer, a magenta dye developer and a yellow dye developer. The dye developer may be utilized in the silver halide emulsion stratum, for example in the form of particles, or it may be disposed in a stratum behind the appropriate silver halide emulsion strata. Each set of silver halide emulsion and associated dye developer strata may be separated from other sets by suitable interlayers, for example, by a layer or stratum of gelatin or polyvinyl alcohol. In certain instances, it may be desirable to incorporate a yellow filter in front of the green-sensitive emulsion and such yellow filter may be incorporated in an interlayer. However, where desirable, a yellow dye developer of the appropriate spectral characteristics and present in a state capable of functioning as a yellow filter may be so employed and a separate yellow filter omitted.

Particularly useful products for obtaining multicolor dye developer images are disclosed in U.S. Pat. No. 3,415,644. This patent discloses photographic products wherein a photosensitive element and an image-receiving element are maintained in fixed relationship prior to exposure, and this relationship is maintained as a laminate after processing and image formation. In these products, the final image is viewed through a transparent (support) element against a light-reflecting, i.e., white background. Photoexposure is made through said transparent element and application of the processing composition provides a layer of light-reflecting material to provide a white background. The light-reflecting material (referred to in said patent as an "opacifying agent") is preferably titanium dioxide, and it also performs an opacifying function, i.e., it is effective to mask the developed silver halide emulsions so that the transfer image may be viewed without interference therefrom, and it also acts to protect the photoexposed silver halide emulsions from postexposure fogging by light passing through said transparent layer if the photoexposed film unit is removed from the camera before image-formation is completed.

U.S. Pat. No. 3,647,437 is concerned with improvements in products and processes disclosed in said U.S.

Pat. No. 3,415,644, and discloses the provision of light-absorbing materials to permit such processes to be performed, outside of the camera in which photoexposure is effected, under much more intense ambient light conditions. A light-absorbing material or reagent, preferably a pH-sensitive phthalein dye, is provided so positioned and/or constituted as not to interfere with photoexposure but so positioned between the photo-exposed silver halide emulsions and the transparent support during processing after photoexposure as to absorb light which otherwise might fog the photoexposed emulsions. Furthermore, the light-absorbing material is so positioned and/or constituted after processing as not to interfere with viewing the desired image shortly after said image has been formed. In the preferred embodiments, the light-absorbing material, also sometimes referred to as an optical filter agent, is initially contained in the processing composition together with a light-reflecting material, e.g., titanium dioxide. The concentration of the light-absorbing dye is selected to provide the light transmission opacity required to perform the particular process under the selected light conditions.

In a particularly useful embodiment, the light-absorbing dye is highly colored at the pH of the processing composition, e.g., 13-14 , but is substantially non-absorbing of visible light at a lower pH, e.g., less than 10-12. This pH reduction may be effected by an acid-reacting reagent appropriately positioned in the film unit, e.g., in a layer between the transparent support and the image-receiving layer.

The dye developers are preferably selected for their ability to provide colors that are useful in carrying out subtractive color photography, that is, the previously mentioned cyan, magenta and yellow. The dye developers employed may be incorporated in the respective silver halide emulsion or, in the preferred embodiment, in a separate layer behind the respective silver halide emulsion, and such a layer of dye developer may be applied by use of a coating solution containing the respective dye developer distributed, in a concentration calculated to give the desired coverage of dye developer unit area, in a film-forming natural, or synthetic, polymer, for example, gelatin, polyvinyl alcohol, and the like, adapted to be permeated by the processing composition.

Other diffusion transfer products and processes in which the dye developers of the present invention may be utilized are described in U.S. Pat. Nos. 3,573,043 and 3,594,165.

As described previously, the image dye-providing materials of the invention are not restricted to dye developers but rather may include many other types of initially diffusible and initially nondiffusible image dye-providing materials. Thus, for example, an initially diffusible coupling dye which is useful in the diffusion transfer process described in U.S. Pat. No. 3,087,817 may be provided by substituting one or both of the indolinyl groups or the anilino group with a color coupling moiety such as a phenol or naphthol having a free position para to the hydroxyl group. An example of such a coupling dye according to the invention is represented by the formula

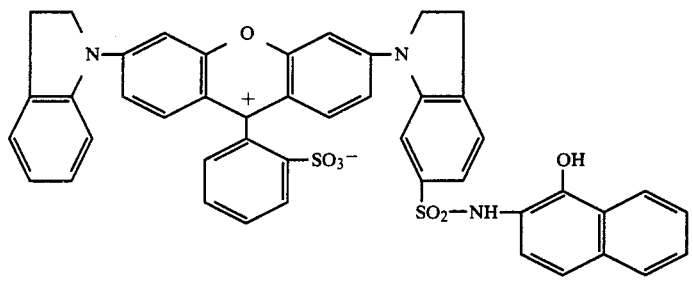

DYE VIII

This dye is initially diffusible but is rendered nondiffusible by coupling with the oxidation product of a color developer, e.g., a p-phenylenediamine or a p-aminophenol, to form a less diffusible product. If the coupling position is substituted by a substituent which renders the dye initially nondiffusible by virtue of a ballast group and which substituent is displaceable upon coupling, such a dye may be employed to provide a diffusible dye where coupling occurs employing the principles described in U.S. Pat. No. 3,227,550.

An initially nondiffusible "redox dye releaser" dye useful in the diffusion transfer process described in U.S. Pat. No. 4,076,529 may be provided by substituting one or both of the indolinyl groups or the anilino group with a sulfonamidophenol or sulfonamidonaphthol group. An example of such a dye according to the invention is represented by the formula

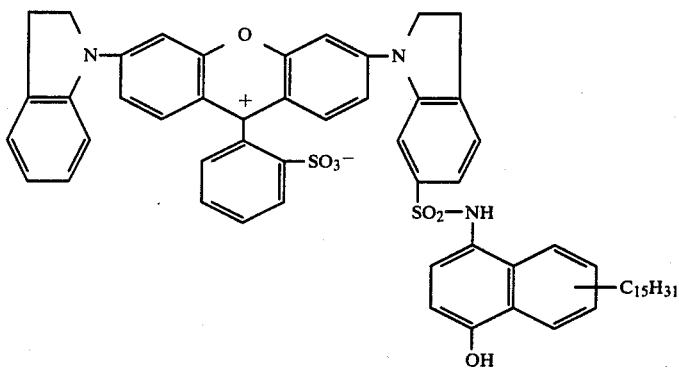

DYE IX

Other sulfonamidophenol and sulfonamidonaphthol groups known in the art, e.g. such as those described in U.S. Pat. Nos. 4,053,312 and 4,055,428, which cleave, in alkaline solution, at the sulfonamido group following oxidation may be used in place of the p-sulfonamidonaphthol group shown above.

Another class of initially nondiffusible image dye-providing materials (described in U.S. Pat. No. 3,433,939) release a diffusible dye following oxidation and intramolecular ring closure. An image dye-providing material of this type according to the invention is represented by the formula

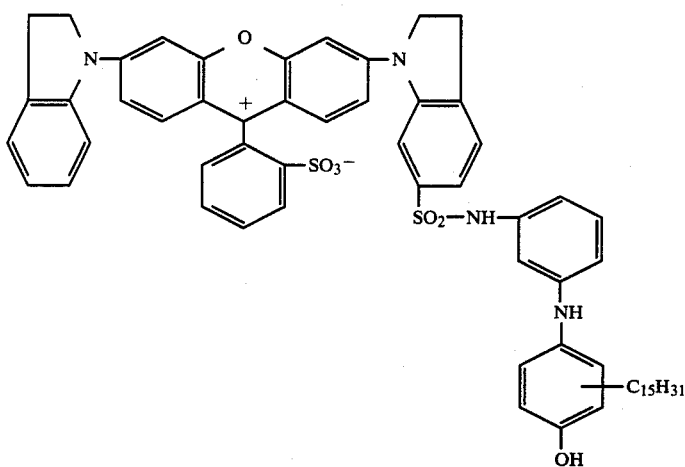

DYE X

Other image dye-providing materials which cleave in alkali following oxidation may be provided by a compound within Formula C wherein Y is —O— or —S— and the hydroquinonyl group contains a ballast group e.g., $C_{15}H_{31}$ in accordance with the disclosure of U.S. Pat. No. 3,725,062. An example of such a compound is represented by the formula It should be understood that although the ballast group in the above illustrated compounds is a long chain alkyl group, other ballast groups known in the art may also be used.

In the use of a nondiffusible image dye-providing material which releases a diffusible image dye-providing material following oxidation in an alkaline environment, the requisite oxidation may be effected by the oxidation product of a mobile developing agent used to develop the photoexposed silver halide emulsion. A particularly effective developing agent for this purpose is 1-phenyl-4,4-dimethyl-3-pyrazolidone; other suitable developing agents are known in the art.

Development is advantageously effected in the presence of an onium compound, particularly a quaternary ammonium compound, in accordance with the disclosure of U.S. Pat. No. 3,173,786. Quaternary ammonium compounds which form an active methylene compound in alkali are especially useful.

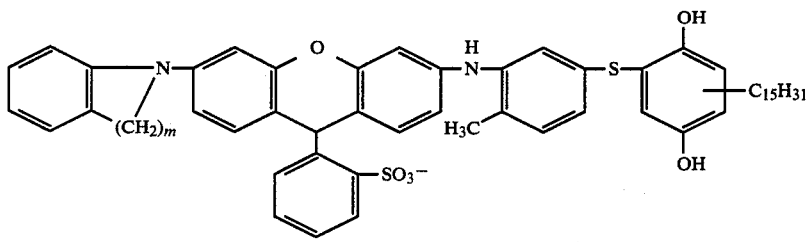

DYE XI

Development may be effected in the presence of a colorless auxiliary or accelerating developing agent such as, for example, a 3-pyrazolidone or a hydroquinone such as 4'-methylphenylhydroquinone, which may be initially arranged in a layer of the photosensitive element or in the processing composition.

In another preferred embodiment of the invention the diffusion control moiety is a thiazolidine group whose cleavage is silver catalyzed. As described in U.S. Pat. No. 3,719,489, image dye-providing materials of this type are photographically inert in the photographic processing composition but are capable of undergoing cleavage in the presence of an imagewise distribution of silver ions and/or soluble silver complex containing silver ions made available as a function of development to liberate a reagent in an imagewise distribution corresponding to that of said silver ion and/or said complex. Dye III is an example of such an image dye-providing material according to the invention.

The invention will now be described further in detail with respect to specific preferred embodiments by way of examples, it being understood that these are illustrative only and the invention is not intended to be limited to the materials, conditions, process parameters, etc., recited therein. All parts and percentages are by weight unless otherwise indicated.

EXAMPLE I 15 gms (0.102 m) of indoline formamide were melted in a 250 ml round bottom flask over a free flame. The melt was cooled in an icebath and swirled as it cooled to distribute the material over the flask as the material solidified. To the flask there were added 34.7 ml of chlorosulfonic acid. The flask was removed from the ice bath and the contents swirled until all the indoline formamide was dissolved (5–10 minutes). The solution was then heated on a steam bath for 10 minutes. The flask was then cooled and the contents slowly poured into 200 ml of ice water cooled in an ice bath. A sticky precipitate was formed which slowly solidified. The precipitate was collected by filtration, dissolved in chloroform and dried over anhydrous calcium sulfate. Evaporation of the filtered chloroform solution gave 16.6 gms. (66% yield) of crude

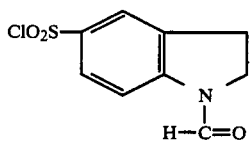

which was then recrystallized from chloroform/petroleum ether.

In 50 ml of pyridine cooled in an ice bath there were dissolved 10 gms (0.035 m) of

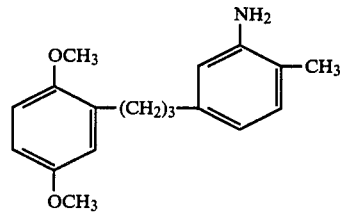

and to the solution there were added 8.6 gms (0.035 m) of the previous product while maintaining the temperature below 20° C. The reaction mixture was stirred overnight. The mixture was poured into dilute HCl and then filtered to collect a gummy residue which is represented by the formula

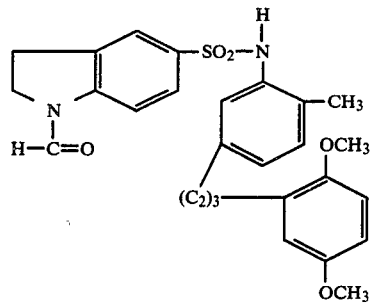

The residue was dissolved in methanol and HCl gas was bubbled through the solution for about 15 minutes. The solution was allowed to stand overnight and the solvent evaporated off under vacuum. An oily residue was obtained which solidified upon standing over two days. The solid was dissolved in chloroform, the solution shaken with aqueous potassium carbonate and the chloroform layer dried over anhydrous calcium sulfate. After evaporation of the chloroform the solid product, represented by the formula

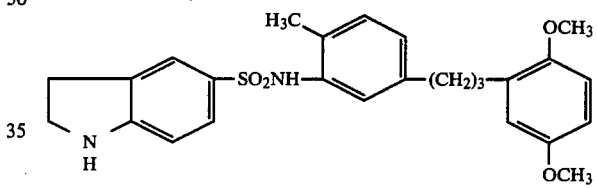

was recrystallized from isopropyl alcohol.

A mixture of 9.0 gms (0.0193 m) of this product, 3.9 gms (0.0096 m) of dichlorosulfonefluorescein, 0.4 gm of magnesium oxide and 10 ml of dimethylsulfoxide was heated with stirring in an oil bath at 135° C. The reaction was monitored by thin layer chromatography (10/90 methanol/chloroform, by volume). After 20 minutes the starting materials had disappeared and TLC showed only one cyan spot. After cooling the reaction mixture slightly, 100 ml of water were added and the solidified dye was filtered off as a blue solid. The solid was washed well with water and dried to give a quantitative yield of a blocked dye developer.

6.0 gms (0.0047 m) of the blocked dye developer were dissolved in 400 ml of chloroform and the solution cooled to $-78°$ C. in a dry ice-acetone bath. To this solution there was added, with stirring, a solution of 12.5 gms (0.05 m) of boron tribromide in 25 ml of chloroform. The mixture was stirred at room temperature overnight and 200 ml of water containing 20 ml of hydrochloric acid were added cautiously. The mixture was stirred and refluxed for one hour. The mixture was then filtered while hot. The resulting blue solid was washed well with water and dried to give 4.8 gms. (85% yield) of dye I, $\lambda max=635$ nm, $\epsilon=85,000$.

To illustrate the utility of the dye developer in photographic applications a film unit was prepared. The negative element of the film unit comprised: a subcoated transparent polyester photographic film base; a cyan dye developer layer comprising about 215 mg./m² of the dye developer represented by dye I and about 215 mg./m² of cellulose acetate hydrogen phthalate; a red sensitive gelatino silver iodobromide (1.075 microns) emulsion layer coated at a coverage of about 538 mg./m² of silver and about 956 mg./m² of gelatin; and an overcoat of about 323 mg./m² of gelatin and about 81 mg./m² of 4'-methylphenylhydroquinone.

The image-receiving element comprised a 4 mil thick transparent subcoated polyethylene terephthalate film base with the following layers coated thereon in succession:

1. as a polymeric acid layer approximately 9 parts of a 1/2 butyl ester of polyethylene/maleic anhydride copolymer and 1 part of polyvinyl butyral coated at a coverage of about 26,372 mgs./m²;
2. a timing layer containing about 4575 mgs./m² of a 60-30-4-6 tetrapolymer of butylacrylate, diacetone acrylamide, styrene and methacrylic acid including about 8% polyvinylalcohol; and
3. a polymeric image receiving layer of: (a) 3 parts of a mixture of 2 parts polyvinylalcohol and 1 part poly-4-vinylpyridine and (b) 1 part of a graft copolymer comprised of 4-vinylpyridine (4VP) and vinylbenzyl trimethylammonium chloride (TMQ) grafted onto hydroxyethyl cellulose (HEC) at a ratio of HEC/4VP/TMQ of 2.2/2.2/1 coated at a coverage of about 3230 mgs./m².

The film unit was processed with a processing composition comprising:

| | GMS/100 cc H₂O |
|---|---|
| Water | 100 cc |
| Polyethylene glycol | 1.23 |
| Colloidal silica | 1.25 |
| N—Hydroxyethyl-N,N',N'—tris carboxymethyl ethylene diamine | 1.89 |
| Lithium nitrate | 0.22 |
| Carboxymethyl cellulose | 2.31 |
| Titanium dioxide | 95.28 |
| Potassium hydroxide | 8.04 |
| Lithium hydroxide | 0.26 |
| N—benzyl-α-picolinium bromide | 2.85 |
| N—phenethyl-α-picolinium bromide | 1.64 |
| Benzotriazole | 1.26 |
| 5-bromo-6-methyl-4-azabenzimidazole | 0.06 |
| Bis-(β-aminoethyl)sulfide | 0.05 |
| 6-methyl uracil | 0.67 |
| 6-benzylamino purine | 0.89 |

The negative was exposed on a sensitometer to a neutral test exposure scale, or step wedge, with red and blue light successively (2 meter-candle-seconds each) and processed by passing the negative and image-receiving elements in superposed relationship, through a pair of rollers at a gap spacing of 0.0020 inch while distributing the processing composition between said elements. The resulting laminate was kept in the dark for 10 minutes to avoid fogging the developing silver halide emulsion by light passing through the transparent film base. When brought into the light a well defined positive cyan image (reflection density to red light $D_{max}=0.90$, $D_{min}=0.28$) was visible through the transparent base of the image-receiving element against the white layer of titanium dioxide provided by the processing composition, without separating the superposed elements.

EXAMPLE II

To a mixture of 60 ml methanol and 30 ml pyridine there were added 12.3 gms (0.0421 m) of

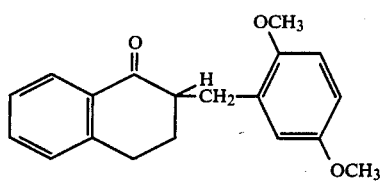

and 12.3 gms (0.176 m) of hydroxylamine hydrochloride and the reaction mixture refluxed for 1 hour on a steam bath. The reaction mixture was poured into 420 ml of water and stirred. A gummy product was obtained from which the water was decanted and another volume of water added. The material continued to be gummy so the water was decanted and the material dissolved in chloroform, extracted once with water and dried. Thin layer chromatography (1/1 ether/petroleum ether, by volume) showed no starting materials present.

Solvent was stripped from the residue under vacuum leaving a semi-solid. Diethyl ether was added to the semi-solid and it was scratched with a glass rod resulting in the formation of a pale yellow solid represented by the formula

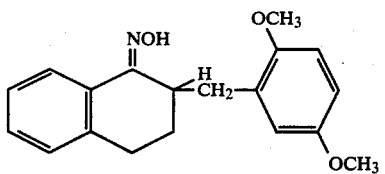

The solid was air-dried to give 2.5 gms.

This product (2.5 gms) and 87.5 gms of polyphosphoric acid were heated at 135° C. for 20 minutes and then poured into 80 ml of water. A yellow solid formed. The solid was collected and recrystallized from tetrahydrofuran. The product is represented by the formula

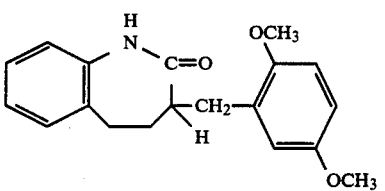

This previous product (1.0 gm, 0.0032 m) and 0.97 g of a 95% borane-dimethyl sulfide mixture was heated on a steam bath for 1½ hours and then allowed to stand over the weekend. The reaction mixture was poured into 100 ml of 5% HCl and heated on a steam bath. The reaction mixture was made basic by the addition of anhydrous potassium carbonate, extracted with diethyl ether and dried. Analysis by thin layer chromatography showed a trace of starting materials. The reduction reaction was repeated to give

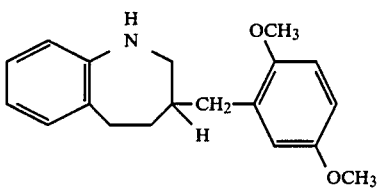

A mixture of 0.8 g (0.0027 m) of this product, 0.57 g (0.0014 m) of dichlorosulfonefluorescein, 0.05 g of magnesium oxide and 29 ml of dimethylsulfoxide was heated at about 135° C. for about 3½ hours. An additional 0.8 g of the previous product was added and heating continued for an additional 2½ hours. The reaction mixture was removed from the steam bath and stored in a nitrogen atmosphere for three days.

More of the previous product was added to the reaction mixture and it was heated again on a steam bath. Sulfanilic acid (0.5 g) was added to the reaction mixture and it was heated for about 1 hour. Thin layer chromatography showed that the orange monochloro-compound was gone. The reaction mixture was added to a water-dilute HCl solution and the dye was collected by filtration and dried. The dye was dissolved in chloroform and eluted from activated magnesium silicate (10/90 methanol/chloroform, by volume). The solvent was evaporated from the pure dye fraction to give the pure dye having the formula

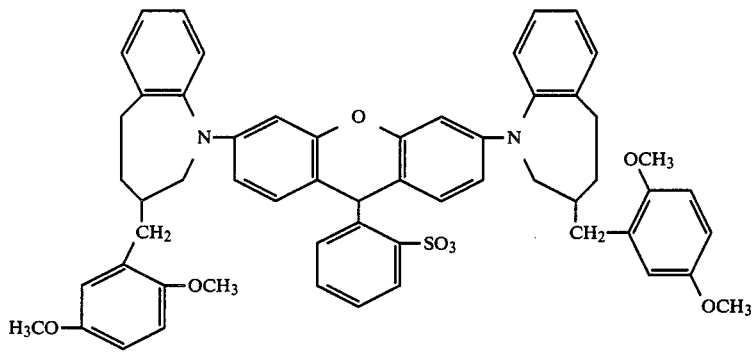

The dye (1.7 g, 0.00183 m) was dissolved in 65 ml chloroform, cooled to −55° C. on a dry ice/acetone bath and to the solution there were added slowly 4.5 g (0.0183 m) of boron tribromide. The reaction mixture was allowed to warm to room temperature and stirred for 4–5 hours. Water and dilute HCl were added to the reaction mixture and it was heated for ½ hour on a steam bath. The dye developer (dye II) precipitated from solution, was collected by filtration, washed by stirring in 5% sodium bicarbonate for 15–30 minutes, collected again by filtration, washed with water and dried. The yield was quantitative. The dye developer exhibited $\lambda_{max}=557$ nm, $\epsilon=84{,}000$ (methyl cellosolve).

A film unit was prepared wherein the negative element comprised a subcoated transparent photographic film base; a magenta dye developed layer comprising about 265 mg./m² of dye developer II and about 265 mg./m² of cellulose acetate hydrogen phthalate, a green sensitive gelatino silver iodobromide (0.61 micron) emulsion layer coated at a coverage of about 807 mg./m² of silver and about 956 mg./m² of gelatin; and an overcoat of about 323 mg./m² of gelatin and about 81 mg./m² of 4'-methylphenylhydroquinone.

The image-receiving element was identical to that described in Example I.

The film unit was processed in the manner described in Example I using the same processing composition with the exception that the exposures of the negative element were to green and blue light successively. There was obtained a well defined magenta image (reflection density to green light $D_{max}=1.81$, $D_{min}=0.40$) which was visible through the transparent base of the image-receiving element.

EXAMPLE III 6.0 gms (0.010 m) of

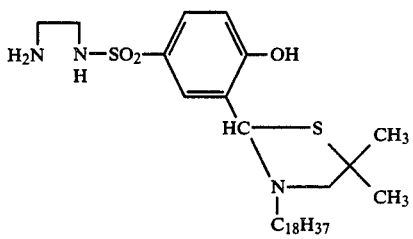

were dissolved in tetrahydrofuran and 1 equivalent (1.0 gm, 0.01028 m) of triethylamine added. To the solution there were added 2.5 gms (0.01028 m) of

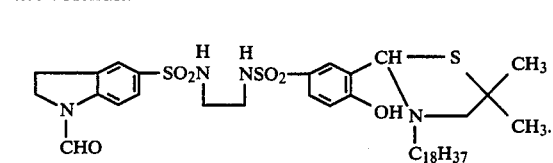

and the mixture was left stirring overnight. Ether (about 50 ml) was added and the solid was filtered off through diatomaceous earth. The solution was evaporated under vacuum to give an oily residue which is represented by the formula The oily residue was dissolved in about 100 ml of methanol. Hydrochloric acid gas was bubbled into the solution for about 10 minutes and the solution was stirred overnight. The solvent was removed under vacuum and subsequently the residue was stirred with diethyl ether and potassium carbonate. The ether layer was isolated and dried over anhydrous calcium sulfate. Thin layer chromatography (5/95 methanol/chloroform, by volume) showed one major spot and several minor spots. The material was collected by filtration and the solvent evaporated off to give 5.0 gms of a compound represented by the formula

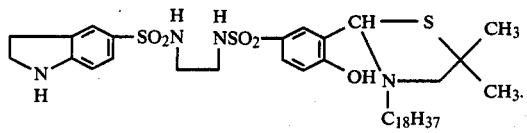

A mixture of 5 gms of this product, 1.4 gms of dichlorosulfonefluorescein, 0.14 gm of magnesium oxide and 10 ml of dimethylsulfoxide was allowed to stand overnight and then heated on a steam bath for three hours. To the reaction mixture there were added 3.0 gms of indolene-5-sulfonic acid and heating was continued for an additional 15 minutes. The reaction mixture was allowed to stand for about two hours, then heated for 15 minutes, poured into water and the solid collected by filtration and air dried. Chromatography on activated magnesium silicate (15/85 methanol/chloroform, by volume) gave 1.5 gms of dye III, $\lambda_{max}=630$ nm, $\epsilon=76,000$.

A film unit was prepared wherein the negative element comprised a subcoated transparent polyester photographic film base; a cyan dye layer coated at a coverage of about 850 mg./m² of dye III and about 850 mg./m² of cellulose acetate hydrogen phthalate; a gelatin layer coated at a coverage of about 646 mg./m²; a blue sensitive gelatino silver iodobromide (1.66 microns) emulsion layer coated at a coverage of about 215 mg./m² of silver and about 646 mg./m² of gelatin, and an overcoat layer containing about 323 mg./m² of gelatin and about 27 mg./m² of succinaldehyde.

The image-receiving element was the same as that described in Example I.

The film unit was processed with a processing composition comprising:

|  | GMS/100 cc H₂O |
| --- | --- |
| Water | 100 cc |
| Sodium hydroxide | 5.0 |
| Methylthiomethyl uracil | 1.5 |
| Thiouracil | 0.009 |
| Titanium dioxide | 50.0 |
| Carboxymethyl hydroxyethyl cellulose | 2.5 |
| Tetramethyl reductic acid | 2.5 |
| Sodium sulfite | 1.0 |

The film unit was processed in the manner described in Example I with the exception that the negative was exposed to the test target with blue light only. After the 10 minute imbibition period the image appeared yellowish and then color shifted to cyan upon standing for 24 hours under ambient conditions. The resultant image was very well defined and had a reflection density to red light $D_{max}=2.72$, $D_{min}=0.33$.

EXAMPLE IV

Under nitrogen atmosphere AlCl₃ (100 g, 0.75 m) was stirred in 200 ml of carbon disulfide while 45 ml (0.62 m) of acetyl chloride were added dropwise. To the mixture there were added slowly 40 g (0.25 m) of

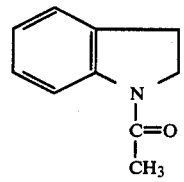

and the mixture mechanically stirred under gentle reflux until the mixture became a gum which could no longer be stirred (about 2 hours). The mixture was then allowed to continue gentle refluxing overnight. After cooling the carbon disulfide was decanted and the flask was allowed to set in the open for several hours. An icewater mixture containing 66 ml of conc. HCl was then poured into the flask and the resulting hydrolyzed product was transferred to a beaker, stirred for a short time, collected by filtration and washed with water. The solid was recrystallized from 2-propanol and dried to give 33 g (65% yield) of

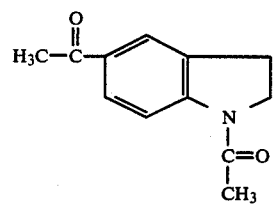

A solution of 18 g (0.089 m) of this product and 9.0 g (0.089 m) of

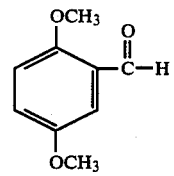

in about 200 ml of ethanol was formed. HCL gas was bubbled into the solution until a solid began to form (about 5 min.). The solution was stirred for an additional 15 minutes, cooled and the solid product collected by filtration and washed with ethanol. The solid was recrystallized from boiling methyl cellosolve to give 7.8 g (35% yield) of

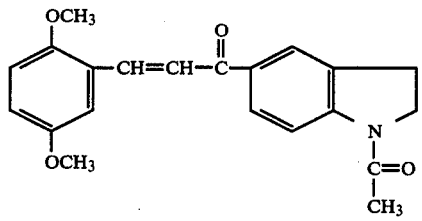

A mixture of 16 g (0.064 m) of this product in about 200 ml of acetic acid with 7 ml of acetic anhydride was reduced under a pressure of 40 psi of hydrogen using 30% Pd/C as catalyst. The reduction was carried out at room temperature until 2 equivalents of hydrogen were taken up followed by heating with steam. The resulting clear liquid mixture was filtered into water and stirred while neutralizing with potassium hydroxide. The white solid which formed

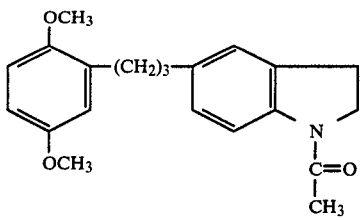

was collected by filtration, washed with water and recrystallized from 2-propanol.

A mixture of 10 g (0.0295 m) of this product in 100 ml of a solution of 25 ml water, 25 ml of conc. HCl and 50 ml of ethanol was refluxed overnight. The resulting solution was made alkaline with potassium hydroxide solution, taken up in ether, dried and the solvent removed to give 7 g (80% yield) of a clear liquid

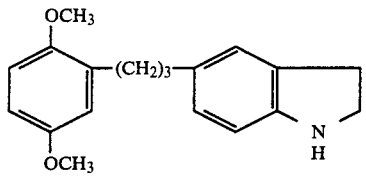

This product (7.0 g, 0.024 m) was dissolved in chloroform and the solution cooled to −78° C. A solution of 7 ml of boron tribromide in 50 ml of chloroform was added dropwise with stirring and the mixture was allowed to reach room temperature and stirred overnight. To the mixture there were added 100 ml of water containing about 10 ml of conc. HCl and the mixture refluxed for 1 hour. The aqueous layer was separated, deaerated with $N_2$ and basicified with 5% $NaHCO_3$ solution. The resulting solid

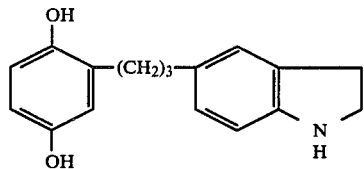

was collected by filtration, washed well with degassed water and allowed to air dry. The yield was 4.8 g (75%).

A mixture of 4.8 g (0.018 m) of this product, 3.4 g (0.008 m) of dichlorosulfone fluorescein and 0.34 g of magnesium oxide was combined with 100 ml of degassed methanol and refluxed with stirring. An immediate formation of a violet adduct occurred. The reaction was followed by thin layer chromatography (10/90 methanol/chloroform, by volume, as eluent). Conversion to the cyan desired product (Dye VII) was incomplete after an 8-hour period. Degassed methyl cellosolve (100 ml) was added and the mixture heated while bubbling in nitrogen gas to drive off methanol. When all the methanol was driven off the mixture was allowed to continue refluxing until the initial violet adduct was gone. The mixture was allowed to cool, and filtered to collect the solid dye developer which was washed well with ether and dried to give 5.0 g (68%) of Dye VII $\lambda_{max}=642$ nm, $\epsilon=71{,}000$.

Although the invention has been described with respect to specific preferred embodiments, it is not intended to be limited thereto but rather those skilled in the art will recognize that variations and modifications may be made therein which are within the spirit of the invention and the scope of the appended claims.

What is claimed is:

1. A compound represented by the formula

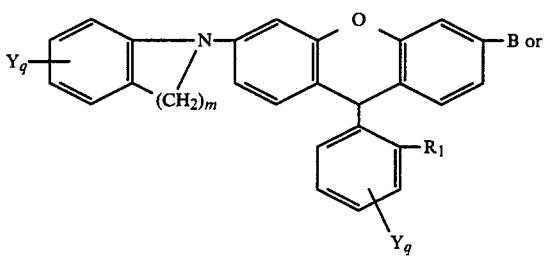

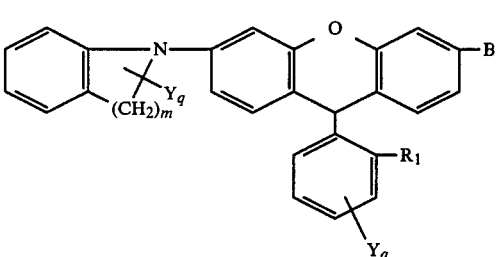

wherein B is 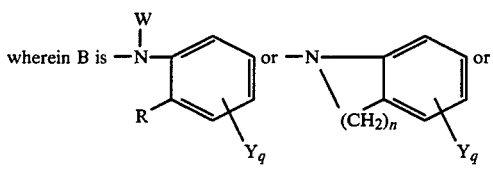

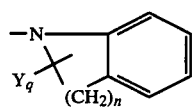

each Y is a substituent having a diffusion control moiety; each q is 0 or 1 provided that at least one q is 1; W is H or alkyl having from 1 to 6 carbon atoms; R is H or alkyl having from 1 to 6 carbon atoms; $R_1$ is H, $-CO_2-$, $SO_3-$ or alkyl having from 1 to 6 carbon atoms; and m and n are each integers of from 2 to 6.

2. The compound as defined in claim 1 wherein $R_1$ is $SO_3^{\ominus}$.

3. A compound as defined in claim 1 wherein said diffusion control moiety D is a hydroquinonyl silver halide developing moiety.

4. A compound as defined in claim 1 wherein said diffusion control substituent Y is the group —E—Dev wherein Dev is a hydroquinonyl group and E is a covalent bond or a divalent linking group.

5. The compound as defined in claim 3 which is represented by the formula

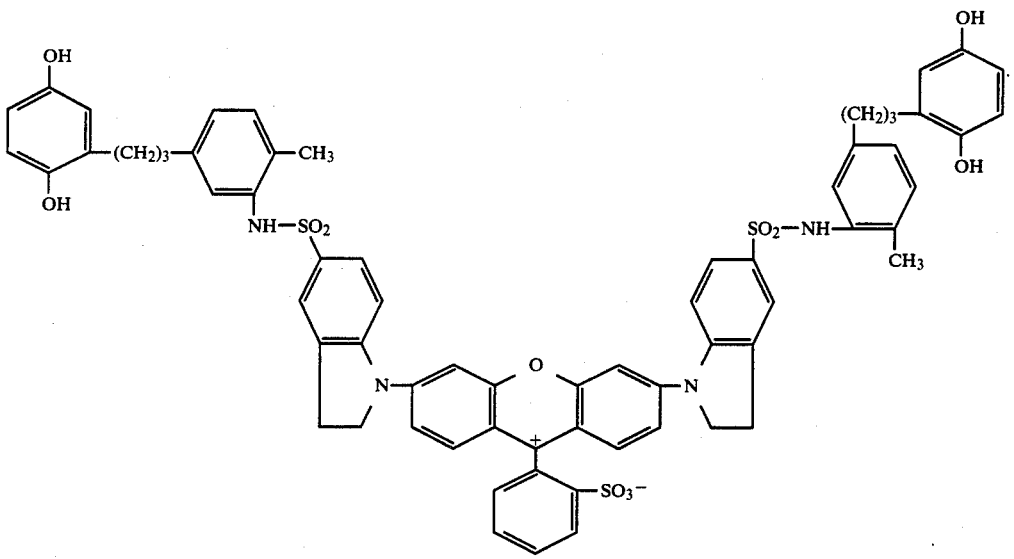

6. The compound as defined in claim 3 which is represented by the formula

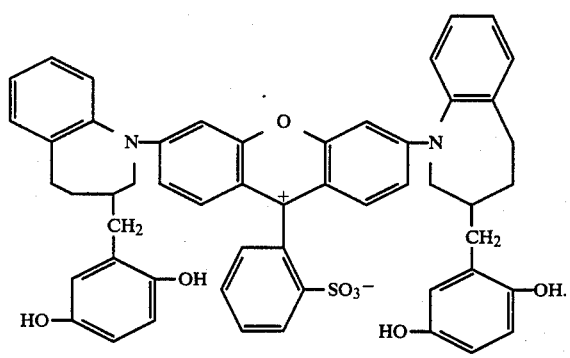

7. The compound as defined in claim 3 which is represented by the formula

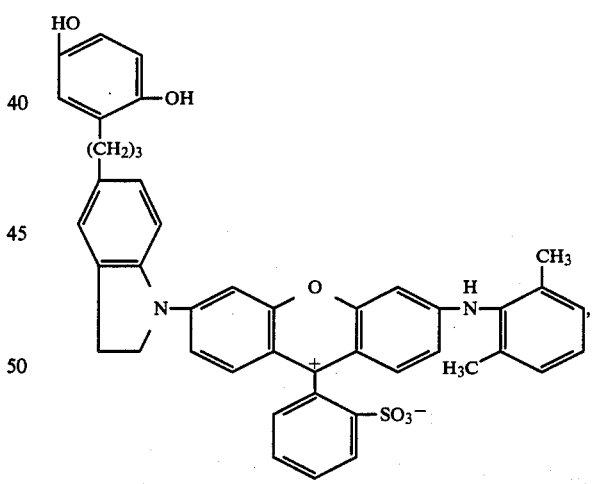

8. The compound as defined in claim 1 wherein said diffusion control moiety D is a color coupling phenol or naphthol moiety having an available coupling position para to the hydroxyl group.

9. The compound as defined in claim 1 wherein said diffusion control moiety D is a sulfonamidophenol group which will cleave or ring close following oxidation.

10. The compound as defined in claim 1 wherein said diffusion control moiety D is a thiazolidine group which is capable of silver-catalyzed cleavage.

11. The compound as defined in claim 10 which is represented by the formula

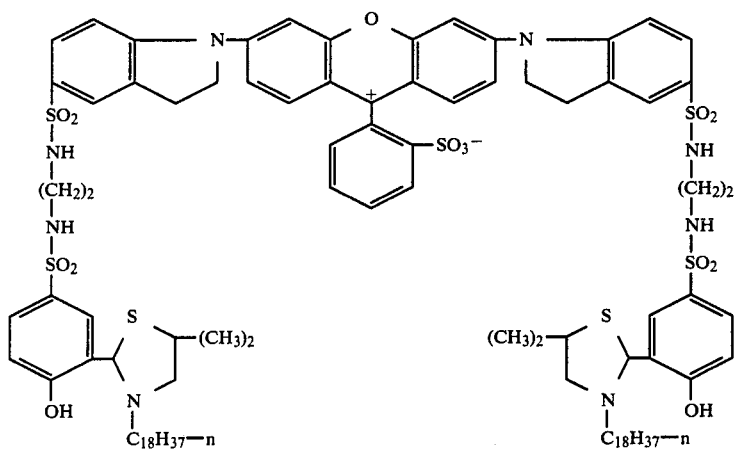

12. A compound represented by the formula

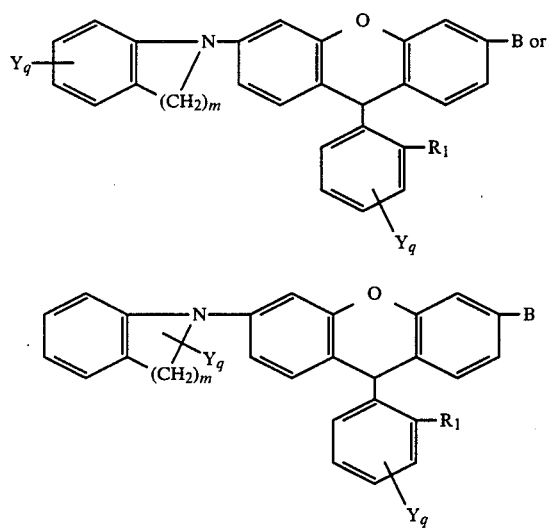

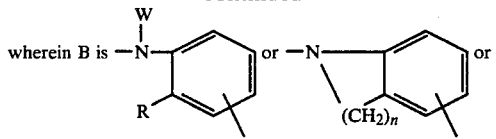

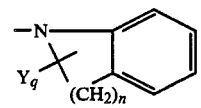

wherein each Y is a substituent containing a diffusion control moiety D, wherein D is selected from the group consisting of a hydroquinonyl silver halide developing moiety, a color coupling phenol or naphthol moiety having an available coupling position para to the hydroxyl group, a sulfonamidophenol group which will cleave or ring close following oxidation and a thiazolidine group which is capable of silver-catalyzed cleavage; each q is 0 or 1 provided that at least one q is 1; W is H or alkyl having from 1 to 6 carbon atoms; R is H or alkyl having from 1 to 6 carbon atoms; $R_1$ is H, $CO_2-$, $SO_3-$ or alkyl having from 1 to 6 carbon atoms; and m and n are each integers of from 2 to 6.

* * * * *